(12) United States Patent
Zhao

(10) Patent No.: US 8,815,286 B2
(45) Date of Patent: Aug. 26, 2014

(54) PHARMACEUTICAL COMPOSITION FOR TREATING HYPERTENSION AND METABOLIC SYNDROME AND USE THEREOF

(75) Inventor: Zhiquan Zhao, Linyi (CN)

(73) Assignee: Lunan Pharmaceutical Group Corporation, Linyi, Shandong Province (CN)

( * ) Notice: Subject to any disclaimer, the term of this patent is extended or adjusted under 35 U.S.C. 154(b) by 377 days.

(21) Appl. No.: 13/055,481

(22) PCT Filed: Jul. 23, 2009

(86) PCT No.: PCT/CN2009/000823
§ 371 (c)(1),
(2), (4) Date: Jan. 24, 2011

(87) PCT Pub. No.: WO2010/009618
PCT Pub. Date: Jan. 28, 2010

(65) Prior Publication Data
US 2011/0118288 A1    May 19, 2011

(30) Foreign Application Priority Data
Jul. 24, 2008  (CN) .......................... 2008 1 0133757

(51) Int. Cl.
| | | |
|---|---|---|
| *A61K 9/20* | (2006.01) | |
| *A01N 43/00* | (2006.01) | |
| *A61K 31/50* | (2006.01) | |
| *A61K 9/48* | (2006.01) | |
| *A61K 31/4184* | (2006.01) | |
| *A61K 45/06* | (2006.01) | |
| *A61K 31/505* | (2006.01) | |
| *A61K 31/519* | (2006.01) | |
| *A61K 31/4439* | (2006.01) | |
| *A61K 31/4178* | (2006.01) | |
| *A61K 9/16* | (2006.01) | |
| *A61K 31/41* | (2006.01) | |
| *A61K 9/00* | (2006.01) | |
| *A61K 9/24* | (2006.01) | |

(52) U.S. Cl.
CPC ........... *A61K 9/4866* (2013.01); *A61K 31/4184* (2013.01); *A61K 45/06* (2013.01); *A61K 31/505* (2013.01); *A61K 31/519* (2013.01); *A61K 31/4439* (2013.01); *A61K 31/4178* (2013.01); *A61K 9/1623* (2013.01); *A61K 31/41* (2013.01); *A61K 9/2059* (2013.01); *A61K 9/485* (2013.01); *A61K 9/0056* (2013.01); *A61K 9/209* (2013.01); *A61K 9/2027* (2013.01); *A61K 9/20* (2013.01); *A61K 9/2054* (2013.01); *A61K 9/1652* (2013.01)
USPC ........................... 424/464; 514/183; 514/247

(58) Field of Classification Search
None
See application file for complete search history.

(56) References Cited

U.S. PATENT DOCUMENTS 6,894,058 B1 *   5/2005   Cameron et al. ............... 514/275

FOREIGN PATENT DOCUMENTS

| CN | 200480002407.2 | 1/2004 |
|---|---|---|
| CN | 101229372 | 7/2008 |

OTHER PUBLICATIONS

Tan, Linda G., et al., Chest, 130 (4_metting Abstracts), (Oct. 1, 2006), pp. 191S.*
Brenner, Barry M., N. Engl J Med, 345 (2001), pp. 861-869.*
Murdock, David K., Wisconsin Medical Journal, vol. 105, No. 5, (2006), pp. 22-25.*
Koh, Kwang Kon, et al., Ciruclation, 110, (2004), pp. 3687-3692.*
Wikipedia, Angiotensin II receptor antagonists, accessed Nov. 8, 2012, pp. 1-7.*
CN 101229372, English Translation, Sep. 1, 2010, pp. 1-9.*
International Search Report, Application No. PCT/CN2009/000823, mailed Oct. 29, 2009.
Wu et al.; "Metabolic Syndrome and Ischemic Cerebrovascular Diseases"; Cerebrovasc Dis Foreign Med Sci (Chinese); May 15, 2005; vol. 13, No. 5, pp. 360-363.
Zhang et al.; "Progress of Blood Pressure Lowering Drugs not Considered Antihypertensives"; Adv. Cardiovasc Dis (Chinese); Nov. 2008, vol. 29, No. 6, pp. 953-956.

* cited by examiner

*Primary Examiner* — Scott Long
*Assistant Examiner* — Lyndsey Beckhardt
(74) *Attorney, Agent, or Firm* — Renner, Otto, Boisselle & Sklar, LLP

(57) ABSTRACT

The present invention provides a pharmaceutical composition comprising the following active ingredients: 1) an angiotensin II receptor antagonist or a pharmaceutically acceptable salt thereof, 2) pioglitazone or a pharmaceutically acceptable salt thereof; and 3) rosuvastatin or a pharmaceutically acceptable salt thereof. The present invention also provides use of the pharmaceutical composition in preparing a medicament for treating hypertension or metabolic syndrome. The pharmaceutical composition of the present invention can treat hypertension or metabolic syndrome, while effectively controlling the incidence of associated cardiovascular diseases and more potently improving survival prognosis in hypertensive patients. When blood pressure is lowered to desired level, the risk factors such as cardiovascular diseases are rectified, metabolic disorders and prognosis of patients are improved, and survival rate of hypertensive patients is raised.

9 Claims, No Drawings

PHARMACEUTICAL COMPOSITION FOR TREATING HYPERTENSION AND METABOLIC SYNDROME AND USE THEREOF

This application is a national phase of the International Application No. PCT/CN2009/000823 filed Jul. 23, 2009, which claims foreign priority to China Application No. CN 200810133757.2 filed Jul. 24, 2008.

TECHNICAL FIELD

The present invention relates to the pharmaceutical field, and specifically relates to a pharmaceutical composition and use thereof in preparing a medicament for treating hypertension and metabolic syndrome.

BACKGROUND ART

Hypertension mainly impairs the blood vessels of humans, rendering arterial angiosclerosis and arteriarctia, which are generally called "arteriosclerosis". When hypertension is combined with diabetes mellitus, the damage to blood vessels would become accelerated and more severe, and the conditions of patients would be worsened rapidly, to which active treatment should be applied. Hypertension is one of the most common cardiovascular diseases, and is closely related to some of the most fatal human diseases, such as coronary heart disease, cerebrovascular diseases, etc. Although the incidence of hypertension in China is not as high as that in Western countries, it increases year by year. With the improvement of living standards and the degradation of the environment, the number of patients suffered from cardiovascular diseases such as hypertension, hyperlipemia and hypercholesterolemia keeps increasing. According to the report, the number of hypertension patients in China has reached 150 million by the end of 2003, and increases at a rate of 5 million per year. Great attention has been paid all over the world to the researches on hypertension, ranging from pathogenesis to clinical prevention and treatment of the disease.

Angiotensin II receptor antagonists are the first choice among the antihypertensive drugs, which have a novel antihypertensive mechanism. It exhibits stable antihypertensive effects, good curative effects, long-term action and good compliance. Sartan drugs include losartan, irbesartan, candesartan, tasosartan, eprosartan, temisartan, valsartan, etc., in which losartan is the first generation of non-peptide angiotensin II receptor inhibitor for oral administration developed by Merck & Co., Inc., and ranks the first among the sartan drugs in the world. Losartan was firstly launched in Sweden in June, 1994, and attained administrative protection in China in 1996. Angiotensin II (AngII) receptor has four subtypes, AT1, AT2, AT3 and AT4, among which AT1 receptor is the overwhelmingly predominant subtype in heart vessels, adrenal cortex and kidney of humans. The medicines currently used in clinical treatment are selective AT1 receptor inhibitors such as losartan, which may block various pharmacological effects produced by endogenous and exogenous AngIIs (including promotion of vasoconstriction, release of aldosterone, etc.), selectively act on AT1 receptors without affecting the functions of other hormone receptors or important ion channels in cardiovascular, or inhibiting angiotensin-converting enzyme (kininase II) that degrades bradykinin, or affecting metabolic processes of AngII and bradykinin. As a first choice of antihypertensive drug, losartan has the advantages of potent effects, long acting term, good compliance, along with renoprotective effects but few adverse effects of dry cough.

Rosuvastatin calcium is a synthesized statin drug which was developed by Shionogi Co., Ltd. (Shionogi Company, Osaka) and assigned to AstraZeneca UK Limited in April, 1998. Rosuvastatin is a selective 3-hydroxyl-3-methylglutaryl-coenzyme A (HMG-CoA) reductase inhibitor, and may be used in the treatment of atheroma, hyperlipemia, familial hypercholesterolemia and similar diseases. The molecular formula of rosuvastatin calcium is shown as follows:

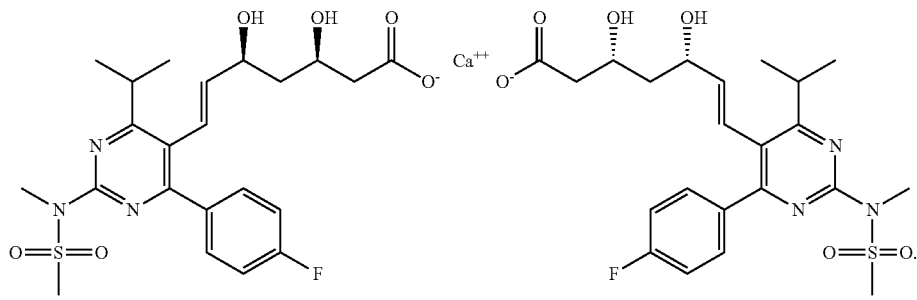 [SMILES: CC(C)c1nc(N(C)S(C)(=O)=O)nc(-c2ccc(F)cc2)c1/C=C/[C@@H](O)C[C@@H](O)CC(=O)[O-] ; [Ca+2] ; CC(C)c1nc(N(C)S(C)(=O)=O)nc(-c2ccc(F)cc2)c1/C=C/[C@@H](O)C[C@@H](O)CC(=O)[O-]]

In view of the clinically testing results and the comparison data among statins, rosuvastatin calcium is indeed a "super statin", which has extremely good antilipemic effects, and is so far the most potent antilipemic drug.

Chinese patent application CN200480002407.2 discloses use of a composition comprising telmisartan and atorvastatin in preparing a medicament for preventing or treating cardiovascular, cardiopulmonary or renal diseases.

According to the report of "Effect of Valsartan and Atorvastatin on Intima-Media Thickness of Common Carotid Artery in Patients with Hypertension", *Acta Aacademiae Medicinae Qingdao Universitatis*, Issue 2, 2005, valsartan combined with atorvastatin is more effective than valsartan alone in reversing carotid artery intima-media thickness in primary hypertension patients.

Although the combination of the mentioned sartans and statins could bring both antihypertensive and antilipemic effects as described in the above patent application and document, these effects are not sufficient for hypertensive patients who may have high risk of cardiovascular diseases, as chronic hypertension may result in damages to key organs such as cardiovascular system and kidney. Accordingly, the objective of antihypertensive treatment is not only to reduce the blood pressure to desired level, but also to rectify the coexisting risk factors such as cardiovascular diseases. Meanwhile, a suitable medicament shall be selected to improve metabolic disorders and prognosis of the patients. Therefore, it is desired in clinical treatment to find a multidrug combination therapy which could treat hypertensive diseases, while effectively controlling the incidence of associated cardiovascular diseases, and more potently improving the survival and prognosis of hypertensive patients.

SUMMARY OF THE INVENTION

The objective of the present invention is to provide a novel pharmaceutical composition for treating hypertension or metabolic syndrome, while effectively controlling the incidence of associated cardiovascular diseases, and more potently improving the survival and prognosis of hypertensive patients. While the blood pressure is reduced to desired level, the coexisting risk factors such as cardiovascular diseases are rectified, metabolic disorders and prognosis of the patients are improved, and the survival rate of the hypertensive patients is increased.

The present invention provides a pharmaceutical composition, which comprises the following active ingredients:
1) an angiotensin II receptor antagonist or a pharmaceutically acceptable salt thereof;
2) pioglitazone or a pharmaceutically acceptable salt thereof; and
3) rosuvastatin or a pharmaceutically acceptable salt thereof.

In the present invention, the angiotensin II receptor antagonist may be selected from losartan, irbesartan, candesartan, tasosartan, eprosartan, temisartan and valsartan.

In one embodiment of the present invention, the molar ratio of the angiotensin II receptor antagonist or a pharmaceutically acceptable salt thereof, pioglitazone or a pharmaceutically acceptable salt thereof, and rosuvastatin or a pharmaceutically acceptable salt thereof in the pharmaceutical composition of the present invention is 1: (0.01~4.3):(0.004~1.54).

Preferably, the molar ratio of the angiotensin II receptor antagonist or a pharmaceutically acceptable salt thereof, pioglitazone or a pharmaceutically acceptable salt thereof, and rosuvastatin or a pharmaceutically acceptable salt thereof in the pharmaceutical composition of the present invention is 1: (0.01~1.5): (0.005~0.5).

In one embodiment of the present invention, the pharmaceutical composition of the present invention comprises the following active ingredients:
1) losartan or a pharmaceutically acceptable salt thereof;
2) pioglitazone or a pharmaceutically acceptable salt thereof; and
3) rosuvastatin or a pharmaceutically acceptable salt thereof.

In one embodiment of the present invention, the weight ratio of losartan or a pharmaceutically acceptable salt thereof, pioglitazone or a pharmaceutically acceptable salt thereof, and rosuvastatin or a pharmaceutically acceptable salt thereof is 1: (0.01~4):(0.01~3.5), wherein the weight of the pharmaceutically acceptable salts of losartan is calculated as losartan, the weight of the pharmaceutically acceptable salt of pioglitazone is calculated as pioglitazone, and the weight of the pharmaceutically acceptable salt of rosuvastatin is calculated as rosuvastatin.

Preferably, the weight ratio of losartan or a pharmaceutically acceptable salt thereof, pioglitazone or a pharmaceutically acceptable salt thereof, and rosuvastatin or a pharmaceutically acceptable salt thereof is 1: (0.02~1):(0.02~1), wherein the weight of the pharmaceutically acceptable salt of losartan is calculated as losartan, the weight of the pharmaceutically acceptable salt of pioglitazone is calculated as pioglitazone, and the weight of the pharmaceutically acceptable salt of rosuvastatin is calculated as rosuvastatin.

In one embodiment of the present invention, the pharmaceutically acceptable salt of pioglitazone in the pharmaceutical composition of the present invention is preferably pioglitazone hydrochloride.

In one embodiment of the present invention, the pharmaceutically acceptable salt of rosuvastatin in the pharmaceutical composition of the present invention is preferably rosuvastatin calcium.

In view of recent progress of clinical research in antihypertensive therapy and the trend of the development of hypertensive diseases, the present invention inventively introduces pioglitazone, an anti-diabetes drug, into the existing antihypertensive therapy and achieves extraordinary treatment effects. The experiments demonstrate that the pharmaceutical composition of losartan, pioglitazone and rosuvastatin according to the present invention not only exhibits significant antihypertensive benefits, but also effectively reduces the damage to key organs such as cardiovascular system and kidney caused by chronic hypertension, effectively rectifies the risk factors such as cardiovascular diseases, improves metabolic disorders and prognosis of the patients, and achieves good and unexpected synergistic effects in the treatment and control of various cardiovascular complications caused by hypertension. The determination results of cardiac hypertrophy and carotid intima-media thickness in rats demonstrate that the pharmaceutical composition provided by the present invention can reverse cardiac hypertrophy and effectively control the incidence of cardiovascular diseases, which proves its advantages in prevention and treatment of cardiovascular diseases. The determination results of urinary microalbumin in rats demonstrate that the pharmaceutical composition of the present invention has renoprotective effects, and can effectively delay the damage to the kidney of hypertension patients.

It has been confirmed by a great deal of experimental researches that combined administration of one of irbesartan, candesartan, tasosartan, eprosartan, temisartan and valsartan, or a pharmaceutically acceptable salt thereof with pioglitazone or a pharmaceutically acceptable salt thereof, and rosuvastatin or a pharmaceutically acceptable salt thereof can also reverse cardiac hypertrophy in rats, exhibit remarkable antihypertensive effects, effectively reduce the damage to key organs such as cardiovascular system and kidney caused by chronic hypertension, effectively rectify the risk factors such as cardiovascular diseases, reduce urinary microalbumin, and protect kidney from damage caused by hypertension. Meanwhile, it can also improve metabolic disorders and exhibit certain effects in the treatment of metabolic syndrome.

Accordingly, the present invention provides a use of the pharmaceutical composition of the present invention in preparing a medicament for treating hypertension or metabolic syndrome.

The present invention also provides a method for treating hypertension or metabolic syndrome with the pharmaceutical composition of the present invention, which comprises administration of an effective amount of the pharmaceutical composition of the present invention to a patient in need of such treatment.

The present invention also provides a pharmaceutical composition as described above for treating hypertension or metabolic syndrome.

The term "metabolic syndrome" refers to a pathological condition in which several metabolic disorders coexist in one single patient. In the present invention, metabolic syndrome includes obesity (abdominal obesity), insulin resistance, impaired glucose regulation, diabetes mellitus, hypertension, dyslipidemia, microalbunminuria and hyperuricemia, etc.

The pharmaceutical composition of the present invention can effectively reduce total cholesterol (TC), high-density lipid cholesterol (HDLC), glycated hemoglobin (HbAlC), fasting blood glucose (FBG), fasting insulin (FINS) and fibrinogen (Fg) in patients with metabolic syndrome, effectively control associated symptoms of cardiovascular diseases, and reduce invalidism rate and fatality rate.

The term "effective amount" refers to a dosage of the pharmaceutical composition that could produce desired treatment effects in a patient.

The pharmaceutical composition of the present invention can be formulated into a solid pharmaceutical formulation, such as tablets, capsules, granules, pills, dripping pills, etc., depending on the properties of the drug and the requirements of convenient administration for the patients. Said tablets include general tablets, coated tablets, sugar-coated tablets, film-coated tablets, enteric-coated tablets, effervescent tablets, chewable tablets, multi-layered tablets, disintegrating tablets, dispersible tablets, sublingual tablets, buccal tablets, implant tablets, soluble tablets, sustained-release tablets, etc. The solid pharmaceutical formulation is employed in the present invention since it has the advantages of convenient carrying and usage, simple and feasible administration route, and good compliance of the patients.

In one embodiment of the present invention, the pharmaceutical composition of the present invention may be in the form of, but not limited to, tablets, capsules or granules.

The pharmaceutical composition of the present invention can be formulated following traditional techniques with the addition of traditional additives such as excipients (e.g., lactose, sucrose, glucose, mannose, sorbitol, starch, dextrin, crystalline cellulose, arabic gum, dextran, etc.), lubricants (magnesium stearate, calcium stearate, talc powder, micronized silica gel, boric acid, sodium dodecylsulfate, etc.), binders (hydroxypropyl cellulose, hydroxypropyl methyl cellulose, polyvinylpyrrolidone, polyethylene glycol, etc.), disintegrating agents (low-substituted hydroxypropyl cellulose, carboxymethyl cellulose, carboxymethyl starch, cross-linked polyvinylpyrrolidone, etc.), emulsifiers (bentonite, magnesium hydroxide, aluminum hydroxide, sodium dodecylsulfate, etc.), stabilizers (methyl p-hydroxybenzoate, benzyl alcohol, phenylethyl alcohol, phenol, sorbic acid, dehydroacetic acid, etc.), flavoring agents (sucrose, flavors, aspartame, cyclodextrin, etc.), diluents, etc.

Additionally, the pharmaceutical composition of the present invention can also be formulated into sustained-release tablets according to the requirements of the patients, so as to regulate blood pressure effectively and safely, maintain a relatively stable plasma drug concentration and longer acting term by slow release, and have the advantages of reduced toxicity and side effects and convenient administration.

The sustained-release tablets prepared from the pharmaceutical composition of the present invention uses cellulose derivatives or vinyl polymer as the sustained-release matrix, wherein the matrix may be one or more of methyl cellulose, hydroxymethyl cellulose, hydroxyethyl cellulose, hydroxypropyl cellulose, hydroxypropyl methyl cellulose, carboxymethyl cellulose, carboxyethyl cellulose, microcrystalline cellulose, starch, polyvinylpyrrolidone and acrylic resin.

The advantages of the pharmaceutical composition according to the present invention lie in the following aspects:

1. The present invention inventively introduces pioglitazone, an anti-diabetes drug, or a pharmaceutically acceptable salt thereof into the existing antihypertensive therapy, and achieves very good synergetic antihypertensive effects. The combined administration of sartans, angiotensin II receptor antagonists, or a pharmaceutically acceptable salt thereof, with pioglitazone, an HMG-CoA reductase inhibitor, or a pharmaceutically acceptable salt thereof, and rosuvastatin or a pharmaceutically acceptable salt thereof exhibits good synergetic antihypertensive effects in experimental researches and clinical observations.

2. The pharmaceutical composition significantly reduces the incidence and degree of adverse effects. The tri-drug combination administration of an antihypertensive drug+an antihyperglycemic drug+an antilipemic drug results in significant synergetic effect in the treatment of hypertension, which significantly reduces the administration dosage, and significantly reduces the incidence and degree of adverse effects as well.

3. Long-term administration of the pharmaceutical composition of the present invention leads to beneficial effects on the long-term survival rate of hypertension patients. It is the most significative clinical problem addressed by the present invention to provide positive effects on the prognosis of the patients. Traditional antihypertensive drugs do not have good prevention and treatment effects on the complications caused by hypertension, such as brain stocks, kidney damage, coronary heart disease, etc., while the pharmaceutical composition of the present invention can treat hypertension, while effectively control the incidence of associated cardiovascular diseases, further improve the survival and prognosis of hypertension patients, reduce the blood pressure to desired level in the antihypertensive treatment, rectify the coexisting risk factors such as cardiovascular diseases, improve metabolic disorders and prognosis of the patients, and increase the survival rate of hypertension patients.

4. The pharmaceutical composition of the present invention has various applications. Due to the synergetic effect, the present invention is suitable for various types of hypertension patients, especially patients with stroke-prone hypertension and hypertension-combined kidney damage. Additionally, the present invention also exhibits good effects on hypertension-combined coronary heart disease and angina, peripheral vascular disease, senile hypertension, gestational hypertension and resistant hypertension.

5. The pharmaceutical composition of the present invention achieves desired effects in the treatment of metabolic syndrome, which has high morbidity in the current society.

DETAILED DESCRIPTION

Hereinafter, the invention will be explained in more detail with the following examples. However, the scope of the present invention is not limited thereto. Any changes and modifications that are obvious for those skilled in the art are intended to be included within the scope of the present invention. All references cited herein are hereby entirely incorporated to the description by reference.

Note: As for each component of the pharmaceutical composition in the following examples, the weight percentage of pioglitazone hydrochloride is calculated as pioglitazone, and the weight percentage of rosuvastatin calcium is calculated as rosuvastatin.

Example 1

Common Tablets

| | |
|---|---|
| Rosuvastatin calcium | 5 g |
| Losartan | 50 g |

| -continued | |
|---|---|
| Pioglitazone hydrochloride | 5 g |
| Starch | 140 g |
| Dextrin | 120 g |
| 50% Ethanol | Appropriate amount |
| Magnesium stearate | 1.0 g |

Manufacture process: Prescribed amounts of rosuvastatin calcium, losartan, pioglitazone hydrochloride, starch and dextrin were weighed and uniformly mixed. To the mixed powder, an appropriate amount of 50% ethanol was added, and uniformly mixed to obtain a soft material, which was allowed to pass through an 18-mesh nylon screen to prepare wet granules. The wet granules were dried at about 60° C. The moisture content of the dried granules should be controlled below 1.5%. The dried granules were further granulated with a 20-mesh screen, uniformly mixed with magnesium stearate and pressed to obtain the final product.

Example 2

Capsules

| | |
|---|---|
| Rosuvastatin calcium | 1 g |
| Losartan | 50 g |
| Pioglitazone hydrochloride | 1 g |
| Microcrystalline cellulose | 300 g |
| Micronized silica gel | 12 g |

Manufacture process: Prescribed amounts of rosuvastatin calcium, losartan, pioglitazone hydrochloride, microcrystalline cellulose and micronized silica gel were weighed and pulverized, screened with a 100-mesh screen, uniformly mixed, and then directly filled into capsules to obtain the final product.

Example 3

Double-Layer Tablets

| | |
|---|---|
| Rosuvastatin calcium | 25 g |
| Mannitol | 10 g |
| Lactose | 40 g |
| Microcrystalline cellulose | 20 g |
| 6% PVP in 95% ethanol solution | 120 g |
| Magnesium stearate | 2 g |

Manufacture process a: Rosuvastatin calcium was screened with a 100-mesh screen, and mannitol, lactose and microcrystalline cellulose were screened with an 80-mesh screen. Prescribed amounts of rosuvastatin calcium, mannitol, lactose and microcrystalline cellulose were weighed and uniformly mixed, to which an appropriate amount of 6% polyvinylpyrrolidone (PVP) in 95% ethanol solution was added to prepare granules. The granules were dried at 60° C. and the dried granules were screened with a 16-mesh screen. Prescribed amount of magnesium stearate was added to the dried granules.

| | |
|---|---|
| Losartan | 25 g |
| Pioglitazone hydrochloride | 25 g |
| Pregelatinized starch | 50 g |
| Mannitol | 50 g |
| 6% PVP in 95% ethanol solution | 100 g |
| Micronized silica gel | 5 g |

Manufacture process b: Losartan and pioglitazone hydrochloride were screened with a 100-mesh screen, and pregelatinized starch and mannitol were screened with an 80-mesh screen. Prescribed amounts of losartan, pioglitazone hydrochloride, pregelatinized starch and mannitol were weighed and uniformly mixed, to which an appropriate amount of 6% PVP in 95% ethanol solution was added to prepare granules. The granules were dried at 60° C. and the dried granules were screened with a 16-mesh screen. Prescribed amount of micronized silica gel was added to the dried granules.

The granules manufactured from the manufacture processes a and b were pressed with a double-layer pressing machine to obtain double layer tablets.

Example 4

Dispersible Tablets

| | |
|---|---|
| Rosuvastatin calcium | 25 g |
| Losartan | 50 g |
| Pioglitazone hydrochloride | 25 g |
| Calcium carboxymethylcellulose | 15 g |
| Crosslinked polyvinylpyrrolidone | 15 g |
| Microcrystalline cellulose | 140 g |
| 10% Starch slurry | Appropriate amount |
| Magnesium stearate | 6 g |

Manufacture process: Prescribed amounts of rosuvastatin calcium, losartan and pioglitazone hydrochloride were screened with a 100-mesh screen, and calcium carboxymethylcellulose, crosslinked polyvinylpyrrolidone and microcrystalline cellulose were screened with an 80-mesh screen. The above components were uniformly mixed and an appropriate amount of 10% starch slurry was added to prepare granules. Magnesium stearate was added to the granules and the mixture was pressed to obtain the final product.

Example 5

Granules

| | |
|---|---|
| Rosuvastatin calcium | 35 g |
| Losartan | 10 g |
| Pioglitazone hydrochloride | 40 g |
| Starch | 200 g |
| Dextrin | 50 g |
| Sucrose powder | 50 g |
| 80% Ethanol | Appropriate amount |

Manufacture process: Prescribed amounts of rosuvastatin calcium, losartan, pioglitazone hydrochloride, starch, dextrin and sucrose powder were weighed and uniformly mixed. To the mixed powder, an appropriate amount of 80% ethanol was added, and uniformly mixed to prepare a soft material, which was allowed to pass through an 18-mesh nylon screen to prepare wet granules. The wet granules were dried at about 60° C., finished with a 20-mesh screen, and packaged to obtain the final product.

Example 6

Disintegrating Tablets

| | |
|---|---|
| Rosuvastatin calcium | 1 g |
| Losartan | 100 g |
| Pioglitazone hydrochloride | 1 g |
| Crosslinked sodium carboxymethylcellulose | 10 g |
| Microcrystalline cellulose | 100 g |
| Polyvinylpyrrolidone | 20 g |
| 5% PVP in 60% ethanol solution | Appropriate amount |
| Micronized silica gel | 5 g |

Manufacture process: Prescribed amounts of rosuvastatin calcium, losartan and pioglitazone hydrochloride were weighed, granulated in a fluidized bed with microcrystalline cellulose as a filler, crosslinked sodium carboxymethylcellulose and polyvinylpyrrolidone as disintegrating agents, 5% PVP in 60% ethanol solution as a binder and micronized silica gel as a glidant, and then pressed to obtain the final product.

Example 7

Sustained Release Tablets

| | |
|---|---|
| Rosuvastatin calcium | 10 g |
| Losartan | 50 g |
| Pioglitazone hydrochloride | 15 g |
| Hydroxypropylmethyl cellulose | 80 g |
| Polyvinylpyrrolidone | 100 g |
| Lactose | 85 g |
| Micronized silica gel | 100 g |

Manufacture process: Prescribed amounts of rosuvastatin calcium, losartan and pioglitazone hydrochloride were uniformly mixed with prescribed amounts of hydroxypropylmethyl cellulose and lactose. Polyvinylpyrrolidone was then added as a binder to prepare granules, which were dried at 40° C. to 80° C. to obtain dried granules. Prescribed amount of micronized silica was added as a lubricant to the dried granules, uniformly mixed, and pressed to obtain the final product.

Example 8

Treatment Effects of the Pharmaceutical Composition of the Present Invention on Blood Pressure and Cardiac Hypertrophy in Spontaneously Hypertensive Rats 1. Experimental Animals and Animal Groups Eighty-eight spontaneously hypertensive rats (male, body weight (300±20) g, provided by Pharmacological Center for New Medicine of Shandong New Time Pharmaceutical Co., Ltd.) were fed for one week for acclimation, and then randomly divided into eight groups with eleven animals in each group.

Model control group: intragastric administration of same volume of physiological saline;
  P group: 0.5 mg/(kg·d) of pioglitazone;
  L group: 5 mg/(kg·d) of losartan;
  R group: 0.5 mg/(kg·d) of rosuvastatin calcium;
  L+R group: 5 mg/(kg·d) of losartan+0.5 mg/(kg·d) of rosuvastatin calcium;
  P+R group: 0.5 mg/(kg·d) of pioglitazone+0.5 mg/(kg·d) of rosuvastatin calcium;
  L+P group: 5 mg/(kg·d) of losartan+0.5 mg/(kg·d) of pioglitazone;
  Pharmaceutical composition of the present invention: 5 mg/(kg·d) of losartan+0.5 mg/(kg·d) of pioglitazone+0.5 mg/(kg·d) of rosuvastatin calcium;

Each group was given intragastric administration once every day for ten weeks. During the experiment, the diet, survival status and behaviors of the animals were recorded, and the animals were weighed once every day and the doses of administration were adjusted according to the body weights. Animals were sacrificed after ten weeks, and their hearts were taken out to determine the weights of left ventricles and calculate left ventricular indexes.

2. Experimental Methods and Results 2.1 Effects of the Pharmaceutical Composition of the Present Invention on the Blood Pressure of Spontaneously Hypertensive Rats Temperature was controlled between 18° C. and 22° C., humidity was controlled between 45% and 65%, and indoor natural light was used. Tail arterial blood pressure of a conscious rat was measured with Intelligent Non-invasive Blood Pressure Monitor BP-2006A (provided by Beijing Softron Co., Ltd.). Blood pressures were measured five times between two and five hours after intragastric administration in the first week, the third week, the fifth week and the eighth week, respectively. The average value of the blood pressures was used as the blood pressure of the sample.

TABLE 1

Effects of the pharmaceutical composition of the present invention on the blood pressure of spontaneously hypertensive rats ($\bar{X} \pm S$, n = 11) (mmHg)

| Groups | Before treatment | After treatment | | | |
|---|---|---|---|---|---|
| | | First week | Third week | Fifth week | Eighth week |
| Model control group | 169 ± 9.1 | 171 ± 9.1 | 175 ± 8.3 | 176 ± 9.5 | 180 ± 8.0 |
| P group | 172 ± 8.3 | 172 ± 9.5 | 168 ± 8.6 | 171 ± 7.7 | 172 ± 8.4 |
| L group | 171 ± 11.6 | 168 ± 7.9 | 162 ± 8.5 | 155 ± 8.1* | 156 ± 7.2* |
| R group | 168 ± 7.5 | 166 ± 8.3 | 168 ± 10.8 | 170 ± 8.3 | 169 ± 7.7* |
| L + R group | 171 ± 8.5 | 165 ± 9.4 | 160 ± 8.7 | 152 ± 12.8* | 149 ± 8.5** |
| P + R group | 169 ± 8.6 | 166 ± 13.7 | 167 ± 9.4 | 168 ± 8.9 | 167 ± 11.4* |
| L + P group | 172 ± 12.8 | 164 ± 8.1 | 157 ± 13.2 | 150 ± 9.7** | 149 ± 7.0** |

TABLE 1-continued

Effects of the pharmaceutical composition of the present invention on the blood pressure of spontaneously hypertensive rats ($\overline{X} \pm S$, n = 11) (mmHg)

| Groups | Before treatment | After treatment | | | |
|---|---|---|---|---|---|
| | | First week | Third week | Fifth week | Eighth week |
| Pharmaceutical composition of the present invention | 170 ± 7.7 | 158 ± 8.6* | 144 ± 7.1**** | 135 ± 7.0**▼*# | 131 ± 7.9**▼*# |

*p < 0.05, compared with the model control group,
**p < 0.01, compared with the model control group,
▼p < 0.05, compared with the L + P group,
**p < 0.01, compared with the P + R group; and
p < 0.05, compared with the L + R group.

The results indicated that the combination of rosuvastatin, losartan and pioglitazone has a synergetic effect on lowering the blood pressures of spontaneously hypertensive rats. As shown from the data of blood pressures measured in the fifth week and the seventh week, the combined administration of the three drugs exhibited good synergetic effects, no matter the administration of losartan and rosuvastatin in combination with pioglitazone, of pioglitazone and rosuvastatin in combination with losartan, or of losartan and pioglitazone in combination with rosuvastatin.

2.2. Measurements of Heart Weight, Left Ventricle Weight, Body Weight and Left Ventricular Hypertrophy Index (Left Ventricular Weight/Body Weight):

After being sacrificed with 10% potassium chloride (2 mmol/L, 1 ml/rat), the rats were weighed. Heart was taken out and aortas and connective tissues outside of the heart were removed. The heart was cleaned by washing, dried with a filter paper, and weighed. The left ventricular was weighed after the atria were removed, and a ratio of left ventricular weight to body weight was calculated.

TABLE 2

Effects of the pharmaceutical composition of the present invention on cardiac hypertrophy of spontaneously hypertensive rats ($\overline{X} \pm S$, n = 8) (g)

| Groups | Body weight | Left ventricular weight | Left ventricular weight/body weight ($\times 10^{-3}$) |
|---|---|---|---|
| Model control group | 306 ± 14 | 1.03 ± 0.11 | 3.37 ± 0.33 |
| P group | 299 ± 12 | 0.986 ± 0.06 | 3.30 ± 0.25 |
| L group | 301 ± 16 | 0.873 ± 0.10 | 2.90 ± 0.26* |
| R group | 304 ± 15 | 0.960 ± 0.08 | 3.16 ± 0.24* |
| L + R group | 302 ± 15 | 0.846 ± 0.15 | 2.80 ± 0.19** |
| P + R group | 305 ± 13 | 0.946 ± 0.14 | 3.10 ± 0.23 |
| L + P group | 298 ± 16 | 0.820 ± 0.12 | 2.75 ± 0.21** |
| Pharmaceutical composition of the present invention | 303 ± 14 | 0.76 ± 0.09 | 2.51 ± 0.14***▼*# |

*p < 0.05, compared with the model control group,
**p < 0.01, compared with the model control group,
▼p < 0.05, compared with the L + P group,
**p < 0.01, compared with the P + R group; and
p < 0.05, compared with the L + R group.

The results indicated that the combination of rosuvastatin, losartan and pioglitazone could effectively reverse left ventricular hypertrophy in spontaneously hypertensive rats, and the triple combination of rosuvastatin, losartan and pioglitazone has a good synergetic effect in the treatment of cardiac hypertrophy in spontaneously hypertensive rats. Good synergetic effects were achieved by administration of losartan and rosuvastatin in combination with pioglitazone, of pioglitazone and rosuvastatin in combination with losartan, or of losartan and pioglitazone in combination with rosuvastatin.

Example 9

Treatment Effects of the Pharmaceutical Composition of the Present Invention on Urinary Microalbumin and Carotid Intima-Media Thickness of the Carotid Arteries in Spontaneously Hypertensive Rats 1. Experimental Animals and Animal Groups Sixty-four spontaneously hypertensive rats (male, body weight (300±20) g, provided by the Pharmacological Center for New Medicine of Shandong New Time Pharmaceutical Co., Ltd.) were fed for one week for acclimation, and then randomly divided into eight groups with eight rats in each group.

Model control group: intragastric administration of same volume of physiological saline;
P group: 1.5 mg/(kg·d) of pioglitazone;
L group: 5 mg/(kg·d) of losartan;
R group: 1 mg/(kg·d) of rosuvastatin calcium;
L+R group: 5 mg/(kg·d) of losartan+1 mg/(kg·d) of rosuvastatin calcium;
P+R group: 1.5 mg/(kg·d) of pioglitazone+1 mg/(kg·d) of rosuvastatin calcium;
L+P group: 5 mg/(kg·d) of losartan+1.5 mg/(kg·d) of pioglitazone;
Pharmaceutical composition of the present invention: 5 mg/(kg·d) of losartan+1.5 mg/(kg·d) of pioglitazone+1 mg/(kg·d) of rosuvastatin calcium;

Each group was given intragastric administration once every day and fed with high sugar and high fat diets for six months. During the experiment, the diet, survival status and behaviors of the animals were recorded, and the animals were weighed once every day and the doses of administration were adjusted according to the body weights.

2. Experimental Methods and Results 2.1. Measurements of Urinary Microalbumin:

Reagents:
1. 10% (v/v) glacial acetic acid solution (pH 2.8).
2. 0.303 mol/L glycine-glacial acetic acid buffer solution (pH 3.0): 22.72 g of glycine was weighed and diluted with 10% glacial acetic acid solution to 1000 ml, to which 100 mg of NaN₃ was added. The buffer solution can be kept for one year at room temperature after sealed.

3. Bromophenol blue (1.924 mmol/L) stock solution: 257.36 mg of BPB was precisely weighed and dissolved to 200 ml with absolute ethanol. The stock solution can be kept for one year in a refrigerator at 4° C.

4. Bromophenol blue (0.231 mmol/L) developing agent: to 60 ml of BPB stock solution, 2.5 ml Triton X-100 was added, and then diluted to 500 ml with glycine-glacial acetic acid buffer solution. The developing agent can be kept for one year at room temperature after sealed.

Collection and detection of samples: rats were taken out and fed in a metabolic cage at the fourth week, the eighth week, the twelfth week and the sixteenth week, respectively, and twelve-hour overnight urinary collection was performed. Urinary amounts were precisely recorded. 4 ml of urine was sampled, treated with sodium azide, and centrifuged at 2000 r/min for 10 min. Supernatant was collected and stored in a freezer at −20° C. before urinary albumin measurement. 2 ml of stored urine of rat was sampled, and 1 ml developing agent was added and uniformly mixed (avoiding the generation of air bubbles). The absorbance A was determined with a UV spectrophotometer at 600 nm.

TABLE 3

Effects of the pharmaceutical composition of the present invention on urinary microalbumin in spontaneously hypertensive rats ($\bar{X} \pm S$)

| Groups | n | Absorbance A (600 nm) |
|---|---|---|
| Model control group | 8 | 0.6851 ± 0.117 |
| P group | 8 | 0.5714 ± 0.124* |
| L group | 8 | 0.6132 ± 0.130 |
| R group | 8 | 0.5672 ± 0.114* |
| L + R group | 8 | 0.5136 ± 0.108* |
| P + R group | 8 | 0.4925 ± 0.105** |
| L + P group | 8 | 0.4968 ± 0.104** |
| Pharmaceutical composition of the present invention | 8 | 0.3554 ± 0.101**▼*# |

*$p < 0.05$, compared with the model control group,
**$p < 0.01$, compared with the model control group,
▼$p < 0.05$, compared with the L + P group,
**$p < 0.05$, compared with the P + R group; and
$p < 0.01$, compared with the L + R group.

The results indicated that the combination of rosuvastatin, losartan and pioglitazone could decrease urinary microalbumin and protect kidney from the damage caused by hypertension, and the triple combination of rosuvastatin, losartan and pioglitazone has a good synergetic effect on urinary microalbumin of spontaneously hypertensive rats. Good synergetic effects were achieved by administration of losartan and rosuvastatin in combination with pioglitazone, of pioglitazone and rosuvastatin in combination with losartan, or of losartan and pioglitazone in combination with rosuvastatin.

2.2. Measurements of Carotid Intima-Media Thickness of the Carotid Arteries

After the animal was anesthetized and fixed, Even's blue (60 mg/kg) dye was injected via a femoral artery. After 30 minutes, myocardial perfusion was performed with 0.9% physiological saline as a perfusate at a perfusion pressure of 13.3 kPa until the effluent became clear. Then, 4% paraformaldehyde in physiological saline was perfused for 10 minutes for in situ fixation (the perfusion pressure was the same as above). The section of Even's blue-stained carotid artery was taken and further fixed with formalin solution, and three parts, i.e. the front, the middle and the rear parts, respectively, were sampled and embedded in paraffin, and then sliced discontinuously to obtain 8 to 10 layers, which were stained with HE. Three vascular sections were randomly selected and input into a computer image processing system so as to perform a computerized image measurement, thereby calculating the intima-media thickness.

TABLE 4

Effects of the pharmaceutical composition of the present invention on intima-media thickness in spontaneously hypertensive rats ($\bar{X} \pm S$, n = 8)

| Groups | Maximum intima thickness (mm) | Ratio of intima to media thickness |
|---|---|---|
| Model control group | 0.1386 ± 0.0229 | 2.0638 ± 0.4361 |
| P group | 0.0958 ± 0.0217* | 1.8325 ± 0.3182 |
| L group | 0.0926 ± 0.0126* | 1.8055 ± 0.3345 |
| R group | 0.1153 ± 0.0205 | 2.0754 ± 0.4167 |
| L + R group | 0.0793 ± 0.0209** | 1.4236 ± 0.2824* |
| P + R group | 0.0826 ± 0.0256** | 1.7627 ± 0.2996* |
| L + P group | 0.0848 ± 0.0142** | 1.6704 ± 0.2578* |
| Pharmaceutical composition of the present invention | 0.0632 ± 0.0202**▼*# | 1.2106 ± 0.2256**▼*# |

*$p < 0.05$, compared with the model control group,
**$p < 0.01$, compared with the model control group,
▼$p < 0.05$, compared with the L + P group,
*$p < 0.05$, compared with the P + R group; and
$p < 0.05$, compared with the L + R group.

The results indicated that the combination of rosuvastatin, losartan and pioglitazone could effectively improve the intima-media thickness in spontaneously hypertensive rats, and the triple combination of rosuvastatin, losartan and pioglitazone exhibits a good synergetic effect on the carotid intima-media thickness of carotid in spontaneously hypertensive rats. Good synergetic effects were achieved by administration of losartan and rosuvastatin in combination with pioglitazone, of pioglitazone and rosuvastatin in combination with losartan, or of losartan and pioglitazone in combination with rosuvastatin.

Example 10

Treatment Effects of the Pharmaceutical Composition of the Present Invention on Patients Suffered from Metabolic Syndrome 1. General Information Sixth-four metabolic syndrome patients were selected from those received treatment in Linyi People's Hospital from March 2007 to June 2008, and randomly divided into a control group and an experimental group.

Control group: twenty-one males and eleven females, whose ages were between 61 and 72 and whose body mass indexes (BMI) were between 26 and 30;

Experimental group: nineteen males and thirteen females, whose ages were between 62 and 70 and whose body mass indexes (BMI) were between 25.5 and 31;

Before the treatment, all patients were subjected to blood lipids (including total cholesterol (TC), high-density lipid cholesterol (HDLC)) analysis, and detection of glycated hemoglobin (HbAlC), fasting blood glucose (FBG), fasting insulin (FINS) and fibrinogen (Fg).

Patients suffered from metabolic syndrome were selected according to the diagnostic standards for type-II diabetes mellitus and hypertension made by WHO in 1999 and referring to the diagnostic standards for metabolic syndrome made by US National Cholesterol Education Program Adult Treatment Panel (NCEP-ATP III) in 2000, while cases of primary hypertension, heart failure (above grade II), diseases in liver, kidney and blood system and like were excluded.

2. Treatment Strategy:

Patients in the control group were administrated with 15 mg of pioglitazone once every day for eight weeks, and patients in the experimental group were administrated with 50 mg of losartan, 5 mg of pioglitazone and 5 mg of rosuvastatin, i.e. the proportions as described in Example 1, once every day. After eight weeks of continuous treatment, all of the above parameters were re-determined, in which blood glucose was determined with hexokinase method, blood lipid was determined with esterase method, fibrinogen was determined with coagulation method and chromogenic substrate assay, HbAlC was determined with chromatography, and fasting insulin was determined with chemiluminescence immunoassay.

Statistical analysis: SPSS software was employed, and test of significance was performed by using a paired sample t test.

3. Treatment Results:

TABLE 5

Changes of Fg, FINS, HbAlC and TC/HDLC before and after treatment ($\overline{X} \pm S$)

| Parameters | Before treatment | | After treatment | |
|---|---|---|---|---|
| | Control group | Experimental group | Control group | Experimental group |
| FBG (mmol/L) | 7.11 ± 2.12 | 7.08 ± 2.09 | 6.69 ± 1.71 | 5.84 ± 1.38*# |
| FINS (mIU/L) | 31.5 ± 8.13 | 32.3 ± 7.96 | 24.36 ± 5.28 | 17.85 ± 5.13*# |
| HbAlC (%) | 6.92 ± 0.61 | 6.87 ± 0.66 | 6.33 ± 0.54 | 5.76 ± 0.56*# |
| TC/HDLC (mmol/L) | 4.25 ± 1.31 | 4.19 ± 1.27 | 3.84 ± 0.81 | 3.11 ± 0.65*# |
| Fg (mg/dl) | 426.3 ± 86.54 | 424.7 ± 84.72 | 390.8 ± 54.82 | 329.4 ± 56.37*# |

*$p < 0.05$, compared with the experimental group before treatment; and
$p < 0.05$, compared with the control group after treatment.

It can be seen from Table 5 that the values of FBG, FINS, HbAlC, TC/HDLC and Fg in the patients suffered from metabolic syndrome before and after treatment with pharmaceutical composition of the present invention show significant differences. Compared with the pioglitazone group, the values of FBG, FINS, HbAlC, TC/HDLC and Fg after treatment with pharmaceutical composition of the present invention also show significant differences. These results indicated that the pharmaceutical composition of the present invention has a reliable and significant treatment effect on metabolic syndrome.

I claim:

1. A pharmaceutical composition, wherein the pharmaceutical composition comprises therapeutically effective amounts of the following active ingredients:
   1) losartan or a pharmaceutically acceptable salt thereof;
   2) pioglitazone or a pharmaceutically acceptable salt thereof; and
   3) rosuvastatin or a pharmaceutically acceptable salt thereof,
   wherein the composition is effective in the treatment of hypertension.

2. The pharmaceutical composition according to claim 1, wherein the weight ratio of losartan or a pharmaceutically acceptable salt thereof, pioglitazone or a pharmaceutically acceptable salt thereof, and rosuvastatin or a pharmaceutically acceptable salt thereof is 1: (0.01~4): (0.01~3.5), wherein the weight of the pharmaceutically acceptable salt of losartan is calculated as losartan, the weight of the pharmaceutically acceptable salt of pioglitazone is calculated as pioglitazone, and the weight of the pharmaceutically acceptable salt of rosuvastatin is calculated as rosuvastatin.

3. The pharmaceutical composition according to claim 2, wherein the weight ratio of losartan or a pharmaceutically acceptable salt thereof, pioglitazone or a pharmaceutically acceptable salt thereof, and rosuvastatin or a pharmaceutically acceptable salt thereof is 1: (0.02~1): (0.02~1), wherein the weight of the pharmaceutically acceptable salt of losartan is calculated as losartan, the weight of the pharmaceutically acceptable salt of pioglitazone is calculated as pioglitazone, and the weight of the pharmaceutically acceptable salt of rosuvastatin is calculated as rosuvastatin.

4. The pharmaceutical composition according to claim 1, wherein the pharmaceutical composition is in a solid dosage form of tablets, capsules or granules.

5. The pharmaceutical composition according to claim 2, wherein the pharmaceutical composition is in a solid dosage form.

6. The pharmaceutical composition according to claim 3, wherein the pharmaceutical composition is in a solid dosage form.

7. A method for treating hypertension or metabolic syndrome, comprising the administration of an effective amount of the pharmaceutical composition according to claim 1 to a patient in need thereof.

8. A method for treating hypertension or metabolic syndrome, comprising the administration of an effective amount of the pharmaceutical composition according to claim 2 to a patient in need thereof.

9. A method for treating hypertension or metabolic syndrome, comprising the administration of an effective amount of the pharmaceutical composition according to claim 3 to a patient in need thereof.

* * * * *